United States Patent [19]
Parker

[11] 4,383,437
[45] May 17, 1983

[54] MONITORING SOLIDS CONTENT OF LIQUID SLUDGES

[75] Inventor: Adrian R. Parker, St. Austell, England

[73] Assignee: Partech (Electronics) Limited, England

[21] Appl. No.: 236,716

[22] Filed: Feb. 23, 1981

[30] Foreign Application Priority Data

Feb. 23, 1980 [GB] United Kingdom ............... 8006196

[51] Int. Cl.³ .......................................... G01N 21/17
[52] U.S. Cl. ........................................ 73/61 R; 356/440
[58] Field of Search ................ 73/61, 61.1 R, 63, 864, 73/864.34; 356/436, 440

[56] References Cited

U.S. PATENT DOCUMENTS

| | | | |
|---|---|---|---|
| 1,970,521 | 8/1934 | Harvey | 73/63 |
| 4,114,427 | 9/1978 | Iguchi | 73/63 |
| 4,245,914 | 1/1981 | Clack | 356/440 |

*Primary Examiner*—S. Clement Swisher
*Attorney, Agent, or Firm*—Thomas J. Greer, Jr.

[57] ABSTRACT

The solids content of a thick sludge is monitored by means of a solids content monitor located in a dilution chamber into which a predetermined quantity of sludge is deposited from a sampling chamber to be diluted by a known factor (e.g. 10) by the addition of water to a predetermined dilution level. Water is sprayed into the sampling and dilution chambers to clean their surfaces and the filling and discharge of the chambers is controlled by solenoid valves operated in an automatic sequence.

10 Claims, 3 Drawing Figures

MONITORING SOLIDS CONTENT OF LIQUID SLUDGES

This invention relates to the monitoring of liquid sludges, and in particular the measurement of the solids content of sludges, that is, the percentage by weight of solid particle content in liquid sludges.

An object of the invention is to provide a method and apparatus for measuring solids content in liquid sludges over a large range of solids content, up to 15% (corresponding to 150,000 mg dry weight of solid matter per liter of water). At the upper end of this solids content range the sludge would have the consistency of thick soup. Methods used for the measurement of the solids content of such sludges, for example ultrasonic beam techniques, are impeded by the inevitable presence in such sludges of air bubbles and occlusions. Furthermore, the high density and solids content of such thick sludges causes fouling of the measuring apparatus, and precludes the practical use of optical apparatus for solids content measurement.

The present invention avoids this difficulty by providing in an automatic cycle for the dilution of a sludge to be monitored to a predetermined controlled extent before making a solids content measurement.

According to the invention in one aspect there is provided a method of monitoring the solids content of liquid sludge comprising the following steps in an automatically controlled sequence:

(a) filling a sampling chamber with the liquid sludge;

(b) discharging the sampling chamber into a dilution chamber when a predetermined volume of sludge is contained in the sampling chamber;

(c) filling the dilution chamber with water to a level which corresponds to a predetermined dilution of the sludge;

(d) measuring the solids content of the diluted sludge by measuring apparatus in the dilution chamber, and (e) cleaning both the sampling chamber and the dilution chamber by spraying clean water into them.

The invention also provides an apparatus for monitoring the solids content of a liquid sludge, comprising a sludge flow duct, a first valve operable to direct sludge from said duct into a sampling chamber having a drain valve, control means for opening the drain valve to drain the sampling chamber into an underlying dilution chamber and to close the first valve when the sludge in the sampling chamber reaches a predetermined level, means for delivering water to the dilution chamber to fill the latter to a level corresponding to a predetermined dilution of the sludge, solids-content measuring apparatus located in the dilution chamber for measuring the solids content of the diluted sludge, a third valve operable to drain the dilution chamber upon completion of the measurement, and means for spraying clean water into both the sampling chamber and the dilution chamber to clean the walls thereof.

The filling of the sampling chamber, the subsequent filling of the dilution chamber, the measurement of the solids content, and the cleaning out of the apparatus, occurs in an automatic sequence, enabling effective measurements of solids content to be made even where the solids content of the sludge is very high. In a typical embodiment of the invention the dilution effected in the dilution chamber would be tenfold—that is, the water added to the sludge in the dilution chamber would be ten times the volume of the sludge obtained from the sampling chamber. Thus if a sludge having a solids content of 15% is to be monitored the dilution chamber will result in a diluted sludge having a solids content of 1.5%, which is capable of measurement using currently available optical instruments for solids content measurement. The measurements made would be multiplied by the dilution factor to obtain an indication of the solids content of the original sludge, such multiplication being made on the output of the measuring instrument, or in the instrument itself.

By sampling sludge from the sludge flow duct at intervals it is possible to monitor the solids content of a liquid sludge, at any desired frequency. The invention finds particular application in monitoring the solids content of sludge in sewage treatment installations. For example, where sewage sludge is to be transported to sea for discharge at sea the solids content of the sludge may be monitored in a collection tank until it reaches a sufficiently high level, when a warning indication may be given by the measuring apparatus.

Preferably the sampling chamber is surrounded by an overflow collecting chamber which drains directly into the sludge flow duct.

The valves in the apparatus may be solenoid-operated and controlled by electrical signals derived from liquid level sensors. For example, the level of sludge in the sampling tank may be monitored by an electrical conduction probe having two contacts which are bridged by the liquid sludge when this reaches the predetermined level in the sampling chamber to provide an output signal controlling operation of the drain valve, draining the sampling chamber into the dilution chamber, and at the same time returning the diverter valve to its non-diverting position.

The means for spraying water into the sampling chamber and the dilution chamber are preferably used both for the dilution of the sludge and, subsequently to the solids content measurement, for the flushing of the apparatus with clean water to clean the internal surfaces of the sampling and dilution chambers prior to the next measurement cycle. The solids-content measuring apparatus may have an associated water spray device for cleaning the surfaces of the measuring apparatus between measuring cycles.

The invention will be further described, by way of example only, with reference to the accompanying purely schematic drawings, in which.

Figure 1:
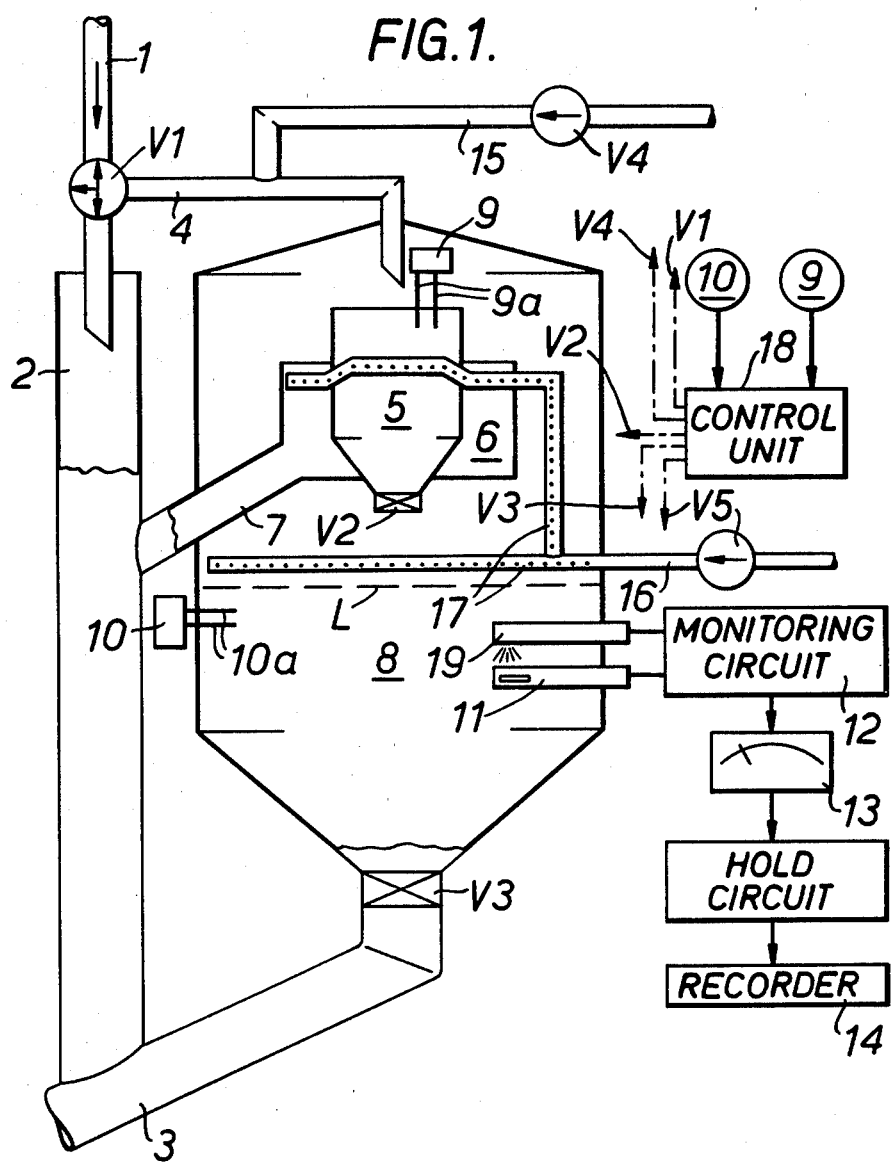
FIG. 1 is a diagrammatic sectional view of an apparatus according to one embodiment of the invention.

Referring first to FIG. 1, a sludge inlet pipe 1 is shown which includes a first solenoid valve V1. The inlet pipe 1 feeds into a vertical sludge flow pipe 2 which in turn leads to a drain pipe 3. In a closed loop sludge monitoring system the drain pipe 3 may lead into a sludge tank the contents of which are to be monitored.

The solenoid V1 is a three-way valve which is normally in the position shown in FIG. 1 allowing sludge to flow from the pipe 1 directly into the sludge flow pipe 2. When enlarged, the solenoid valve V1 is effective to divert liquid sludge from the inlet pipe 1 into a sampling pipe 4 which delivers liquid sludge into a sampling chamber 5. The sampling chamber 5 has a funnel-shaped base terminating at its lower end in a solenoid-operated valve V2 which is normally closed. The sampling chamber 5 is open at its upper end and surrounded by an annular overflow tank 6 which drains through an inclined overflow pipe 7 directly into the sludge flow pipe 2.

The sampling chamber 5 is housed coaxially within a dilution chamber 8, which also has a funnel-shaped base terminating in a normally closed outlet valve V3, also solenoid-operated.

An electrical liquid level sensor 9 is mounted in the sampling chamber 5 at a position clear of contamination by liquid sludge. The sensor 9 has a pair of electrodes 9a which project into the top of the sampling chamber 5 and terminate at free ends which are separated horizontally and disposed at a level corresponding to a predetermined filling level of the sampling chamber 5. When liquid sludge fills the sampling chamber 5 to the predetermined level the sludge bridges the two electrodes 9a, the change in electrical resistance between the electrodes 9a being detected by the sensor 9 which provides an output signal controlling the cyclic operation of the apparatus, as later described.

A second liquid level sensor 10 is located externally of the side wall of the dilution chamber 8 and has a pair of conductive electrodes 10a projecting into the dilution chamber 8 at a level below the level of the outlet valve V2, the sensor 10 providing an output signal when the dilution chamber 8 is filled to a level L indicated in broken outline below the level of the sampling chamber outlet valve V2.

A photoelectric solids content measuring instrument 11 is mounted in a wall of the dilution chamber 8 below the level L and is connected to a monitoring circuit 12. A direct reading instrument 13 and/or a pen recorder 14 may be associated with the monitoring circuit 12.

A supply of clean water, for example a water main, is connected to the sampling pipe 4 through a water supply pipe 15 including a solenoid valve V4. A further water supply pipe 16 is connected to the dilution chamber 8 through a solenoid valve V5 and communicates with spray nozzle manifolds 17 within the dilution chamber 8, the sampling chamber 5 and the overflow chamber 6, as illustrated diagrammatically.

The illustrated apparatus operates in an automatic cycle controlled by a control unit 18. The automatic cycle which has electrical input connections to the level sensors 9 and 10 and electrical output connections to the solenoid valves V1–V5, as shown schematically, would typically be completed at predetermined timed intervals, typically of the order of 5 minutes, controlled by a time switch incorporated in the control unit 18. At the end of each timed interval the following cycle of sequential operations would be initiated by the control unit 18:

(i) the solenoid valve V1 is energised into its diverting position, diverting the liquid sludge from the inlet pipe 1 into the sampling pipe 4 and filling the sampling chamber 5;

(ii) when the level of sludge in the sampling chamber 5 reaches the predetermined level set by the sensor electrodes 9a the sensor 9 provides a trip signal which de-energises the solenoid valve V1, which returns to its non-diverting position (FIG. 1);

(iii) after a predetermined interval (for example, five seconds) the solenoid valve V2 is opened and at the same time the solenoid valves V4 and V5 are opened. The liquid sludge in the sampling chamber 5 is thereupon drained through the open valve V2 into the dilution chamber 8, and the sampling chamber 5 is rinsed by water entering through the inlet pipe 15 and through the spray manifold 17;

(iv) the water fills the dilution chamber 8, diluting the liquid sludge therein, until the level L is reached. Before this level is reached, however, the solenoid valve V4 is closed, under control of a timer, the "topping up" of the dilution chamber 8 being effected by the water sprayed into the chambers through the spray manifold 17;

(v) when the predetermined level L is reached in the dilution chamber 8 the sensor 10 provides an output signal which closes the solenoid valves V2 and V5 and initiates the measurement of solids content by the instrument 11 connected to the circuit 12;

(vi) when the solids content measurement has been completed the solenoid valve V3 is opened, allowing the contents of the dilution chamber 8 to discharge into the drain pipe 3;

(vii) the solenoid valves V4 and V5 are then opened for a period of about 20 seconds to flush the dilution chamber 8 with clean water. During this flushing operation the solenoid valve V2 is open to allow further flushing of the sampling chamber 5 while the valve V4 is open;

(viii) the solenoid valves V2 and V3 are closed and the apparatus is then ready for a further monitoring cycle.

In a typical installation the operating cycle of the apparatus would occupy a time of about 1–2 minutes.

Figure 2:
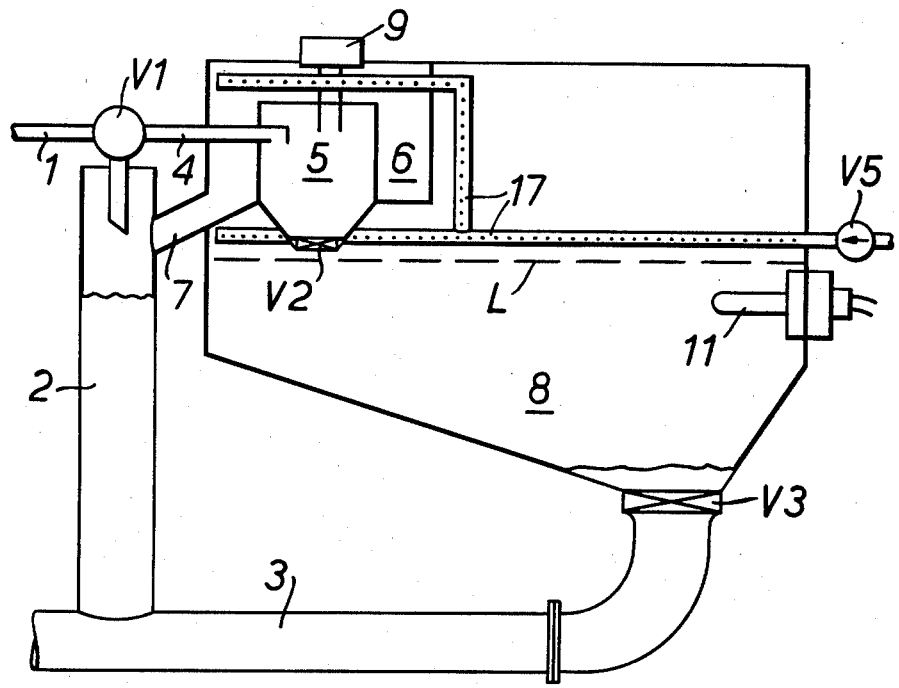
FIG. 2 is a diagrammatic sectional view corresponding to FIG. 1 of another embodiment of apparatus in accordance with the invention.
Figure 3:
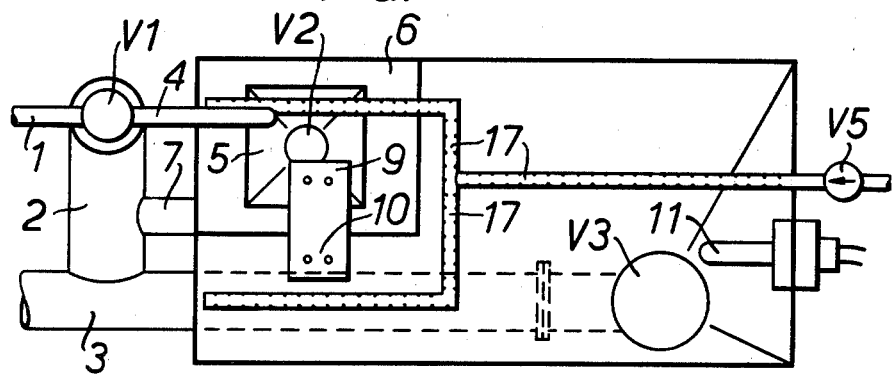
FIG. 3 is a plan view of the apparatus illustrated in FIG. 2.

FIGS. 2 and 3 illustrate a typical practical embodiment, in which the same reference numerals are used to indicate corresponding component parts. It will be seen that the sampling chamber 5 is mounted on one side of the dilution chamber 8, above the liquid level therein, and the level sensors 9 and 10 are grouped together in a common housing.

The solids content measuring instrument 11 may have an associated water spray device 19 (FIG. 1) for cleaning its measuring surfaces. A "hold" circuit may be associated with the measuring apparatus to "memorise" the measurements made by the instrument 11 in each measuring cycle and to initiate alarms or warnings in the event of predetermined threshold measurements being exceeded.

I claim:

1. A method of monitoring the solids content of liquid sludge, comprising the following steps in an automatically controlled sequence:
    (a) filling a sampling chamber with the liquid sludge;
    (b) discharging the sampling chamber into a dilution chamber when a predetermined volume of sludge is contained in the sampling chamber;
    (c) filling the dilution chamber with water to a level which corresponds to a predetermined dilution of the sludge;
    (d) measuring the solids content of the diluted sludge by electronic measuring apparatus having a surface in the dilution chamber, and
    (e) cleaning both the sampling chamber, and the dilution chamber and the measuring apparatus surface by spraying clean water in to them the said chambers.

2. Apparatus for monitoring the solids content of a liquid sludge, comprising:
    a sludge flow duct,
    a sampling chamber,
    a first valve operable to direct sludge from said flow duct into said sampling chamber, a drain valve at the bottom of the sampling chamber,
means responsive to the liquid level in the sampling chamber to close the first valve and open the drain valve when the sludge in the sampling chamber reaches a predetermined level,
a dilution chamber arranged below the sampling chamber to receive sludge from the latter when the drain valve is open,
means for delivering water to the dilution chamber to fill the latter to a level corresponding to a predetermined dilution of the sludge,
solids-content measuring apparatus located in the dilution chamber for measuring the solids content of the diluted sludge,
a third valve operable to drain the dilution chamber, and
means for spraying clean water into the sampling chamber and the dilution chamber to clean the walls thereof.

3. The apparatus defined in claim 2, wherein the sludge flow duct extends vertically and the first valve is a diverter valve operable to divert sludge from said duct into the sampling chamber, the dilution chamber having a drain outlet, through said third valve, leading into the said flow duct.

4. The apparatus defined in claim 2 or claim 3, including control means operable to control an automatic cycle of operations including operation of the first valve, the drain valve, the means for delivering water to the dilution chamber, the third valve and the water spraying means.

5. The apparatus defined in claim 2 or claim 3, including an overflow collecting chamber surrounding the sampling chamber and having a drain connection leading directly into the sludge flow duct.

6. The apparatus defined in claim 2 or claim 3, wherein each of the valves is a solenoid-operated valve.

7. The apparatus defined in claim 2 or claim 3, wherein the means responsive to the liquid level in the sampling chamber comprise an electrical conduction probe having two contacts which are bridged by the liquid sludge when this reaches a predetermined level in the sampling chamber to provide an output signal for controlling operation of the drain valve and of the said first valve.

8. The apparatus defined in claim 2 or claim 3, wherein the means for delivering water to the dilution chamber to fill the latter are constituted by part of said means for spraying clean water, and by a further valve controlling the delivery of water to said spraying means.

9. The apparatus defined in claim 4 wherein the automatic cycle of operations of the control means includes a first spraying of water into the sampling and dilution chambers, when the contents of the sampling chamber are discharged into the dilution chamber, and a second spraying of water into said sampling and dilution chambers when the contents ot the dilution chamber are discharged, both said sprayings being effected with the drain valve open.

10. The apparatus defined in claim 9, wherein the control means control closure of the drain valve before the liquid in the dilution chamber reaches the predetermined dilution level, further filling of the dilution chamber being effected through the spraying means.

* * * * *